United States Patent
Yamamoto et al.

(10) Patent No.: US 9,706,979 B2
(45) Date of Patent: Jul. 18, 2017

(54) MOBILE ULTRASONIC DIAGNOSTIC DEVICE

(71) Applicant: HITACHI ALOKA MEDICAL, LTD., Mitaka-shi, Tokyo (JP)

(72) Inventors: Masa Yamamoto, Mitaka (JP); Yoshinori Hirano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 146 days.

(21) Appl. No.: 14/370,097

(22) PCT Filed: Dec. 7, 2012

(86) PCT No.: PCT/JP2012/081844
§ 371 (c)(1),
(2) Date: Jul. 1, 2014

(87) PCT Pub. No.: WO2013/118383
PCT Pub. Date: Aug. 15, 2013

(65) Prior Publication Data
US 2014/0371592 A1 Dec. 18, 2014

(30) Foreign Application Priority Data

Feb. 6, 2012 (JP) ................................. 2012-022879

(51) Int. Cl.
*A61B 8/00* (2006.01)
*A61B 8/14* (2006.01)

(52) U.S. Cl.
CPC .................. *A61B 8/56* (2013.01); *A61B 8/14* (2013.01); *A61B 8/4427* (2013.01); *A61B 8/461* (2013.01);
(Continued)

(58) Field of Classification Search
CPC ......... A61B 8/14; A61B 8/4427; A61B 8/461; A61B 8/462; A61B 8/465
See application file for complete search history.

(56) References Cited

U.S. PATENT DOCUMENTS 6,310,834 B1 10/2001 Nosaka
6,527,721 B1 3/2003 Wittrock et al.
(Continued)

FOREIGN PATENT DOCUMENTS

CN 1536496 A 10/2004
CN 1602445 A 3/2005
(Continued)

OTHER PUBLICATIONS

International Search Report, dated Mar. 12, 2013, issued in corresponding application No. PCT/JP2012/081844.
(Continued)

*Primary Examiner* — Baisakhi Roy
(74) *Attorney, Agent, or Firm* — Westerman, Hattori, Daniels & Adrian, LLP (57) ABSTRACT

A mobile ultrasonic diagnostic device comprising: a battery (30); a storage processing unit (38) that performs storage processing of data used by the mobile ultrasonic diagnostic device; a high-speed storage unit (80) that performs storage processing faster than the storage processing unit (38); and a storage processing determination unit (36) that determines the storage processing on the basis of the temperature or remaining power of the battery (30). Data can be safely used without loss even when there is the possibility that power cannot be supplied from the battery, as a result of the storage processing unit (38) and the high-speed storage unit (80) performing storage processing on the basis of the storage processing determined by the storage processing determination unit (36).

15 Claims, 9 Drawing Sheets

(52) U.S. Cl.
CPC ............... *A61B 8/462* (2013.01); *A61B 8/54* (2013.01); *A61B 8/465* (2013.01); *A61B 8/546* (2013.01)

(56) References Cited

U.S. PATENT DOCUMENTS

| | | | | |
|---|---|---|---|---|
| 6,542,846 | B1* | 4/2003 | Miller | A61B 8/546 340/584 |
| 2004/0015079 | A1* | 1/2004 | Berger | A61B 8/461 600/437 |
| 2004/0135540 | A1 | 7/2004 | Ogawa | |
| 2005/0228281 | A1* | 10/2005 | Nefos | A61B 8/08 600/446 |
| 2006/0100530 | A1* | 5/2006 | Kliot | A61B 5/0002 600/483 |
| 2006/0265610 | A1 | 11/2006 | Kim | |
| 2008/0205715 | A1 | 8/2008 | Halmann | |
| 2009/0140043 | A1* | 6/2009 | Graves | G06F 19/327 235/380 |
| 2010/0122023 | A1 | 5/2010 | Shih | |
| 2010/0160786 | A1 | 6/2010 | Nordgren et al. | |
| 2010/0284521 | A1* | 11/2010 | McBroom | A61B 6/4233 378/189 |
| 2010/0327766 | A1* | 12/2010 | Recker | H02J 9/02 315/291 |
| 2011/0157233 | A1* | 6/2011 | Kitagawa | G06F 3/011 345/660 |
| 2012/0004545 | A1* | 1/2012 | Ziv-Ari | A61B 8/5207 600/437 |
| 2012/0057767 | A1 | 3/2012 | Halmann | |
| 2012/0078074 | A1* | 3/2012 | Gao | A61B 8/5223 600/350 |
| 2013/0181867 | A1* | 7/2013 | Sturdivant | H04W 64/00 342/368 |

FOREIGN PATENT DOCUMENTS

| | | |
|---|---|---|
| CN | 1866165 A | 11/2006 |
| CN | 101645027 A | 2/2010 |
| CN | 101739309 A | 6/2010 |
| CN | 102135921 A | 7/2011 |
| CN | 102915264 A | 2/2013 |
| JP | 2004-508126 A | 3/2004 |
| JP | 2006-309883 A | 11/2006 |
| JP | 2008-206980 A | 9/2008 |
| JP | 2009-273517 A | 11/2009 |
| JP | 2010-067292 A | 3/2010 |
| JP | 2010067292 A | 3/2010 |
| JP | 2000278871 A | 6/2010 |
| JP | 2010-528697 A | 8/2010 |
| JP | 2011-153952 A | 8/2011 |
| WO | 2008/146208 A2 | 12/2008 |

OTHER PUBLICATIONS

Notification Concerning Transmittal of International Preliminary Report on Patentability (Chapter I of the Patent Cooperation Treaty) forms PCT/IB/338 of International Application No. PCT/JP2012/081844 mailed Aug. 21, 2014 with forms PCT/IB373, PCT/IB/338 and PCT/ISA/237. w/English Translation (17 pages).

Chinese Office Action issued on Aug. 28, 2015 for counterpart Chinese Application No. 201280069174.2, with English translation. (18 pages).

Office Action dated Aug. 16, 2016, issued in counterpart Japanese Patent Application No. 2013-557376, with English translation. (6 pages).

* cited by examiner

MOBILE ULTRASONIC DIAGNOSTIC DEVICE

TECHNICAL FIELD

The present invention relates to a mobile ultrasonic diagnostic device, and particularly to a mobile ultrasonic diagnostic device having an advantage of being conveniently installed in a place (ease of installation).

BACKGROUND ART

Although conventional ultrasonic diagnostic devices are mainly of a wagon type in which various devices are mounted on a movable wagon, mobile ultrasonic diagnostic devices having excellent portability are also on the market. For example, the so-called notebook type mobile ultrasonic diagnostic device has a structure in which a lid chassis with a display device is foldable with respect to a thin body chassis.

Design has been implemented to display, on a display unit, an alarm signal generated based on the comparison result between the battery level of a mobile ultrasonic diagnostic device and a threshold (as cited in, for example, Patent Document 1).

CITATION LIST

Patent Document

Patent Document 1: JP 2009-273517 A

SUMMARY OF THE INVENTION

Technical Problem

Although Patent Document 1 describes that the alarm signal is displayed based on the battery level of the mobile ultrasonic diagnostic device, if electrical power cannot be supplied from the battery when processing is being executed in the mobile ultrasonic diagnostic device, the processing being executed is interrupted and cannot be completed. For example, if data are being transferred to outside the mobile ultrasonic diagnostic device, data transfer cannot be completed. In that case, the mobile ultrasonic diagnostic device is shut down.

Therefore, there is a possibility that currently-running processing cannot be continued, and data are lost while they are being transferred.

An object of the present invention is to provide a mobile ultrasonic diagnostic device which can be used safely without losing data even if there is a possibility that a battery will not be able to supply electrical power.

Solution to Problem

In order to achieve the object of the present invention, in a mobile ultrasonic diagnostic device, storage processing is determined based on the battery temperature or the battery level, and appropriate storage processing is performed based on the determined storage processing.

Advantageous Effects of Invention

The present invention can be used safely without losing data even if there is a possibility that the battery will not be able to supply electrical power.

DESCRIPTION OF EMBODIMENT

Figure 1:
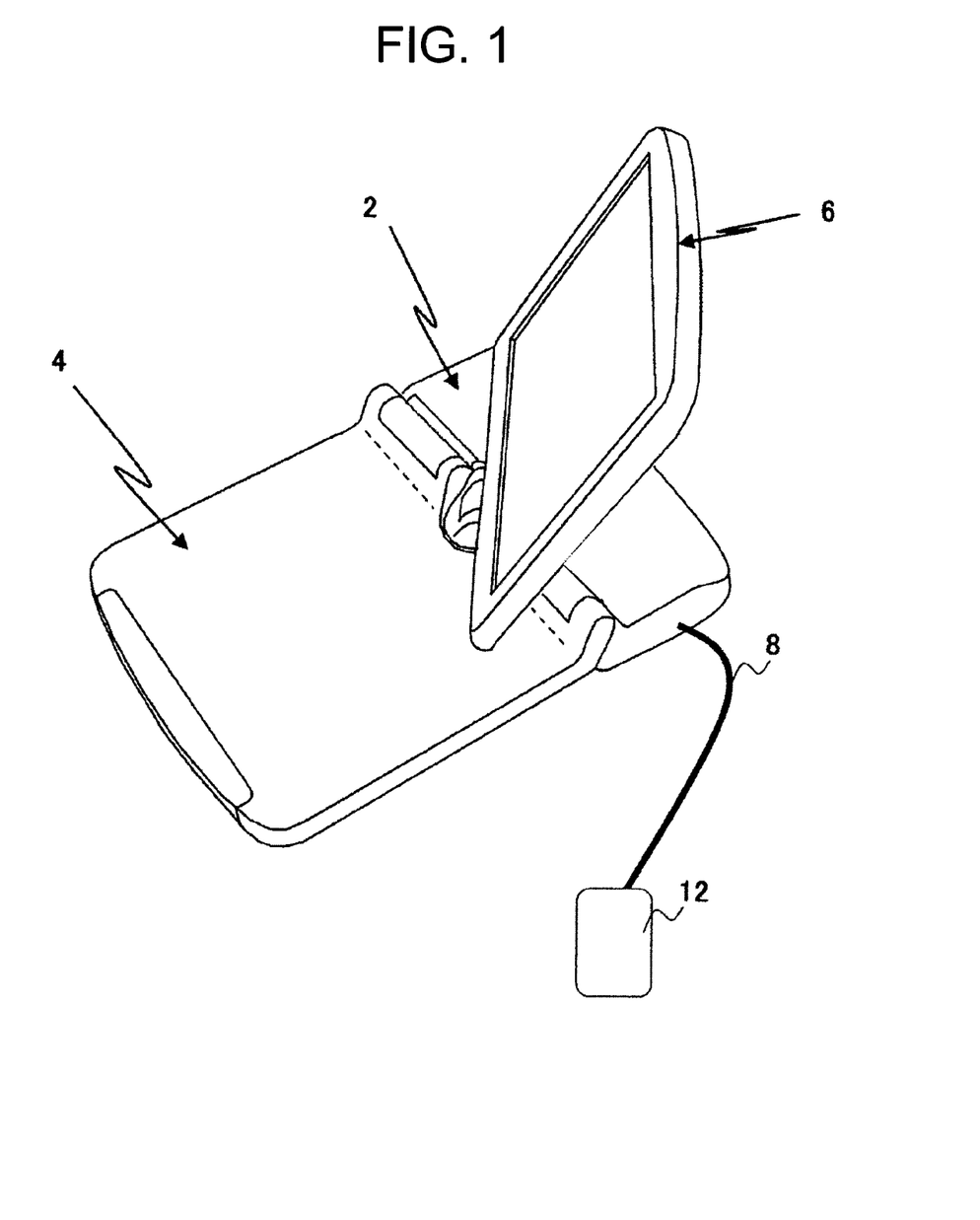
FIG. 1 shows an external view of a mobile ultrasonic diagnostic device according to the present invention.

FIG. 1 shows an external view of the mobile ultrasonic diagnostic device according to the present invention. As shown in FIG. 1, the mobile ultrasonic diagnostic device has, as a structure, a body chassis 2 for storing a device having a main processing function, a keyboard chassis 4 having an operating unit to be operated by an operator, and a display chassis 6 having an image display unit for displaying an image. Further, the body chassis 2 is connected to an ultrasound probe 12 for receiving and transmitting ultrasonic waves, via a cable 8.

Embodiment 1

Figure 2:
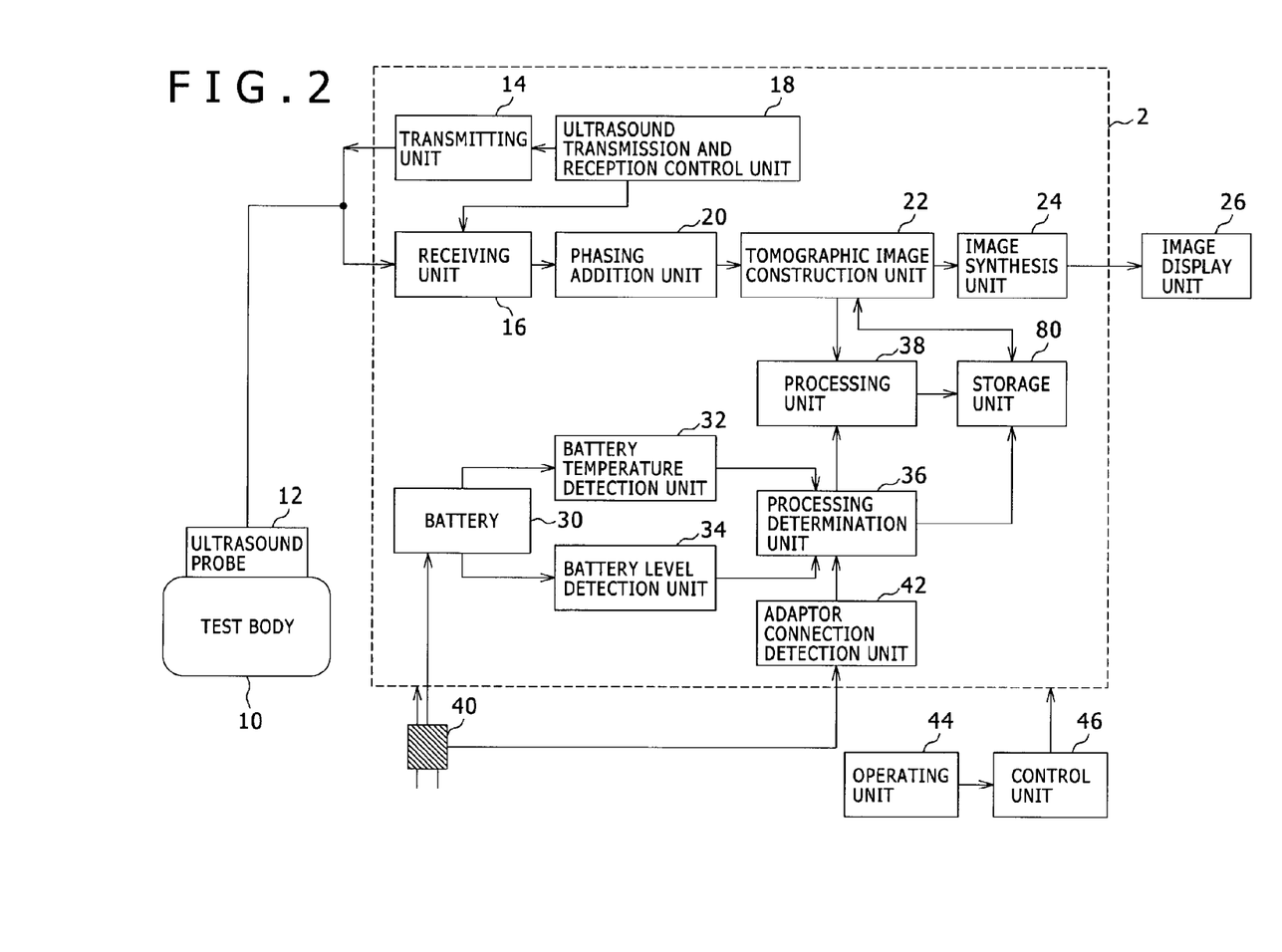
FIG. 2 shows a configuration diagram of the mobile ultrasonic diagnostic device according to the present invention.

FIG. 2 shows a block diagram which illustrates a structure of the mobile ultrasonic diagnostic device. As shown in FIG. 2, the mobile ultrasonic diagnostic device has the ultrasound probe 12 which is placed on a test object 10 for transmitting and receiving ultrasonic waves, a transmitting unit 14 which transmits ultrasonic waves to the test object 10 via the ultrasound probe 12 repeatedly at time intervals, a receiving unit 16 which receives ultrasonic waves reflected from the test object 10 as a reflection echo signal, a ultrasound transmission and reception control unit 18 which controls the transmitting unit 14 and the receiving unit 16, and a phasing addition unit 20 which phases and adds the reflection echo signals based on the ultrasonic waves received by the receiving unit 16.

In addition, the mobile ultrasonic diagnostic device has a tomographic image construction unit 22 which constructs a tomographic image, such as a black and white tomographic image, of the test object 10 based on RF frame data which are generated by phased addition in the phasing addition unit 20, an image processing unit 24 which adjusts the tomographic image to be displayed on an image display unit 26, and processes the image by, for example, superimposing it with other images or displaying those images parallel to each other, to thereby synthesize the images, and the image display unit 26 which displays the image output from the image processing unit 24. The image processing unit 24 also performs processing such as trimming and image conversion on the image.

Further, the mobile ultrasonic diagnostic device has a battery 30 which supplies electrical power to components constituting the mobile ultrasonic diagnostic device, a battery temperature detection unit 32 which detects the temperature of the battery 30, a battery level detection unit 34 which detects the battery level of the battery 30, an AC adaptor 40 which supplies electrical power to the components and charges the battery 30, and an adaptor connection detection unit 42 which detects that the AC adaptor 40 is connected to an electric outlet, and that the AC adaptor 40 supplies electrical power to the components or that the AC adaptor 40 charges the battery 30.

The components are those constituting the mobile ultrasonic diagnostic device and mainly include the numbered elements in FIG. 2 (such as the transmitting unit 14, the receiving unit 16, the ultrasound transmission and reception control unit 18, the phasing addition unit 20, the tomographic image construction unit 22, and the image processing unit 24).

In addition, the mobile ultrasonic diagnostic device has a storage processing determination unit 36 which determines storage processing based on the temperature or the battery level of the battery 30, a storage processing unit 38 which performs storage processing of data used in the mobile ultrasonic diagnostic device, and a high-speed storage unit 80 which performs storage processing faster than the storage processing unit 38, and the storage processing unit 38 and the high-speed storage unit 80 perform storage processing based on the storage processing determined by the storage processing determination unit 36.

Still further, the mobile ultrasonic diagnostic device has an operating unit 44, and a control unit 46 which transfers control information to the components based on an instruction received from the operating unit 44.

Next, the components of the mobile ultrasonic diagnostic device will be further described in detail below. The ultrasound probe 12 is formed by arranging a plurality of vibrators, and has a function of transmitting and receiving ultrasonic waves to/from the test object 10 via the vibrators.

The transmitting unit 14 has a function of generating wave transmission pulses for driving the ultrasound probe 12 and generating ultrasonic waves, and a function of setting the convergence point of the transmitted ultrasonic waves at a certain depth. In addition, the receiving unit 16 amplifies the reflection echo signal which is based on ultrasonic waves received by the ultrasound probe 12 with a predetermined gain, to thereby generate an RF signal which is a received wave signal. The phasing addition unit 20 receives, as an input, the RF signal amplified in the receiving unit 16, performs phase control on the signal, forms ultrasonic beams directed to one or more convergence points, and generates RF frame data.

The tomographic image construction unit 22 receives, as an input, the RF frame data from the phasing addition unit 20, and performs signal processing, such as gain compensation, log compression, wave detection, contour enhancement, and filter processing, to thereby construct a tomographic image.

The operating unit 44 is composed of a keyboard having various keys, a track ball, etc. Rotating the track ball of the operating unit 44 enables, for example, the control unit 46 to adjust a range of a display area of the tomographic image. Then, pressing the enter key on the keyboard of the operating unit 44 enables the control unit 46 to confirm the adjusted area. The control unit 46 then transmits location information of the set display area to the image processing unit 24. The image processing unit 24 causes the image display unit 26 to display the tomographic image based on the display area.

The AC adaptor 40 receives, as an input, AC power and outputs a predetermined amount of electrical power. The AC adaptor 40 has the function of charging the battery 30 and the function of supplying electrical power to the components. When the AC adaptor 40 is connected to the electric outlet, the AC adaptor 40 is electrically connected to the components and the battery 30.

The battery temperature detection unit 32 has a function of detecting the temperature of the battery 30. More specifically, the battery temperature detection unit 32 is adhered to a predetermined object on the surface of the battery 30 and detects the temperature of cells. The battery level detection unit 34 has a function of detecting the battery level of the battery 30. More specifically, the battery level detection unit 34 measures the remaining voltage of the battery 30, thereby detecting the battery level of the battery 30. The battery temperature detection unit 32 and the battery level detection unit 34 may be installed in the battery 30.

Figure 3:
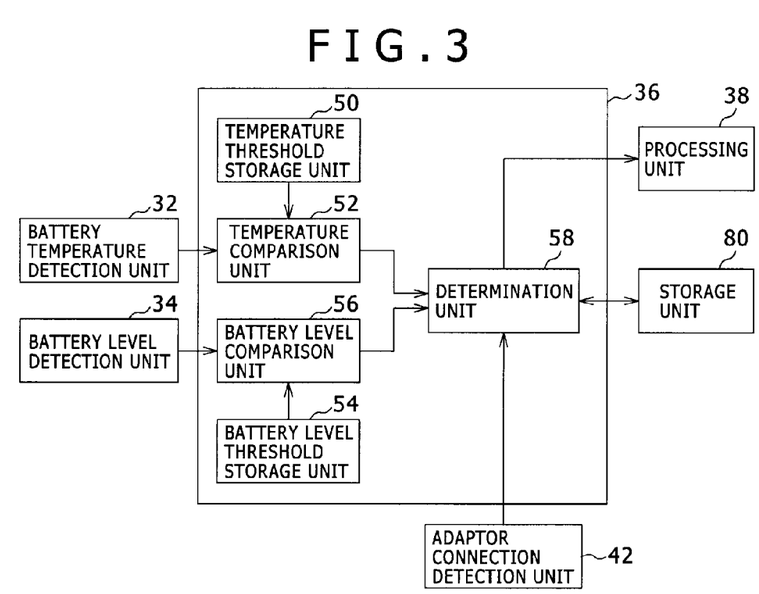
FIG. 3 shows a configuration diagram of a storage processing determination unit 36 of the present invention.

Next, the storage processing determination unit 36 will be explained by reference to FIG. 3. The storage processing determination unit 36 has a temperature threshold storage unit 50 for storing a temperature threshold for the battery 30, a temperature comparison unit 52 for comparing the temperature threshold stored in the temperature threshold storage unit 50 with the temperature of the battery 30 detected by the battery temperature detection unit 32 which detects the temperature of the battery 30, a battery level threshold storage unit 54 for storing a battery level threshold for the battery 30, a battery level comparison unit 56 for comparing the battery level threshold stored in the battery level threshold storage unit 54 with the battery level of the battery 30 detected by the battery level detection unit 34 which detects the battery level of the battery 30, and a determination unit 58 for determining storage processing based on the temperature or the battery level of the battery 30.

Figure 4:
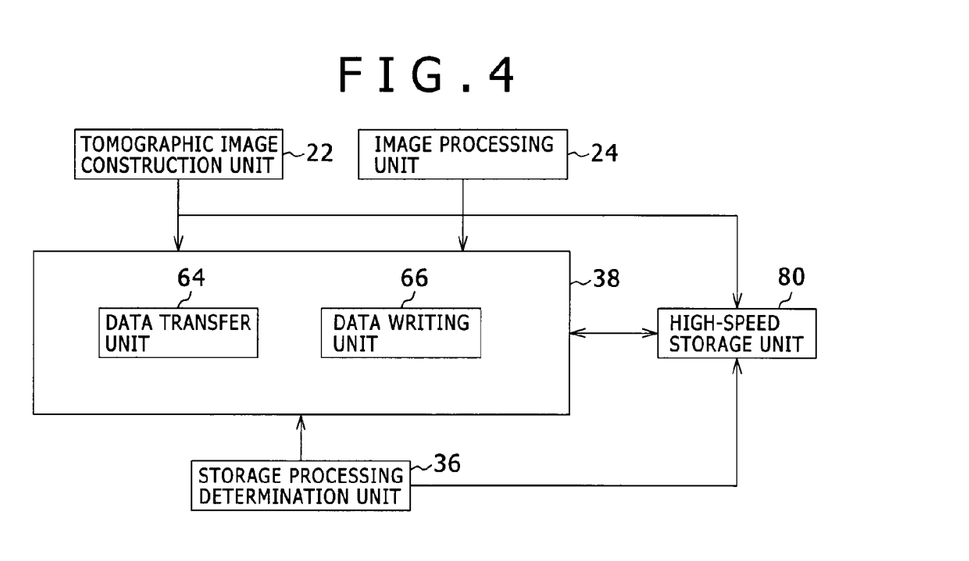
FIG. 4 shows a configuration diagram of a storage processing unit 38 of the present invention.

The storage processing unit 38 will be explained by reference to FIG. 4. The storage processing unit 38 has a function of performing storage processing of data used in the mobile ultrasonic diagnostic device. The high-speed storage unit 80 has a function of performing storage processing of data faster than the storage processing unit 38. The data used in the mobile ultrasonic diagnostic device is a concept which encompasses all of RF frame data generated in the phasing addition unit 20, tomographic image data constructed in the tomographic image construction unit 22, processed image data constructed in the image processing unit 24, three-dimensional volume data composed of the tomographic image data, measurement data measured using the tomographic image data and the processed image data, test body information data for identifying the test body 10, image rendering information data for identifying image rendering conditions by the control unit 46, etc.

The storage processing unit 38 has at least one of a data transfer unit 64 for transferring data to devices outside the mobile ultrasonic diagnostic device and a data writing unit 66 for writing data into a predetermined storage medium.

The data transfer unit 64 has a function of transferring data to the devices outside the mobile ultrasonic diagnostic device via network communication of the Internet or an intranet. Those devices outside the mobile ultrasonic diagnostic device include ultrasound diagnostic devices other than the mobile ultrasonic diagnostic devices from which the data are transferred, PCs, and network storage devices.

The data writing unit 66 has a function of writing data into a predetermined storage medium. The storage medium into which the data are written by the data writing unit 66 is a storage medium such as a CD, a DVD, a BD, a USB memory, or a USB hard disk. The data writing unit 66 writes the data into one of a CD, a DVD, a BD, a USB memory, and a USB hard disk.

The high-speed storage unit 80 has a storage medium which performs storage processing faster than the storage processing unit 38. In other words, the storage medium of the high-speed storage unit 80 performs storage processing faster than storage processing which is written by the data writing unit 66 and storage processing which is externally transferred by the data transfer unit 64. In addition, the storage medium of the high-speed storage unit 80 has a larger capacity than the storage medium into which data are written by the data writing unit 66. The storage medium of the high-speed storage unit 80 is a storage medium, such as a build-in flash SSD memory or a built-in hard disk.

The storage processing determination unit 36 determines storage processing based on the temperature or the battery level of the battery 30, and the control unit 46 causes the storage processing unit 38 and the high-speed storage unit 80 to perform storage processing based on the storage processing determined in the storage processing determination unit 36.

When the storage processing determination unit 36 determines that the temperature or the battery level of the battery 30 is in a normal state, the storage processing unit 38 can perform storage processing of data transfer or data writing. Data transfer or data writing in the storage processing unit 38 takes a relatively long time. Storage processing of data transfer or data writing in the storage processing unit 38 sometimes takes T minutes or more (for example, 5 minutes or more). Unless the temperature or the battery level of the battery 30 is in the normal state, there is a possibility that the battery 30 runs down while storage processing of data transfer or data writing is being continued. Therefore, the storage processing unit 38 cannot perform storage processing of data transfer or data writing unless the temperature or the battery level of the battery 30 is in the normal state.

Further, if the storage processing determination unit 36 determines that the temperature or the battery level of the battery 30 is not in the normal state; that is, determines that it is in an abnormal state, the high-speed storage unit 80 performs storage processing. The storage processing in the high-speed storage unit 80 is processing which takes less time than storage processing of data transfer or data writing in the storage processing unit 38. The storage processing in the high-speed storage unit 80 is processing which takes less than T minutes (for example, less than 5 minutes). Therefore, if the temperature or the battery level of the battery 30 is not in the normal state, the storage processing unit 38 stops storage processing of data transferor data writing, and the high-speed storage unit 80 performs storage processing.

Figure 5:
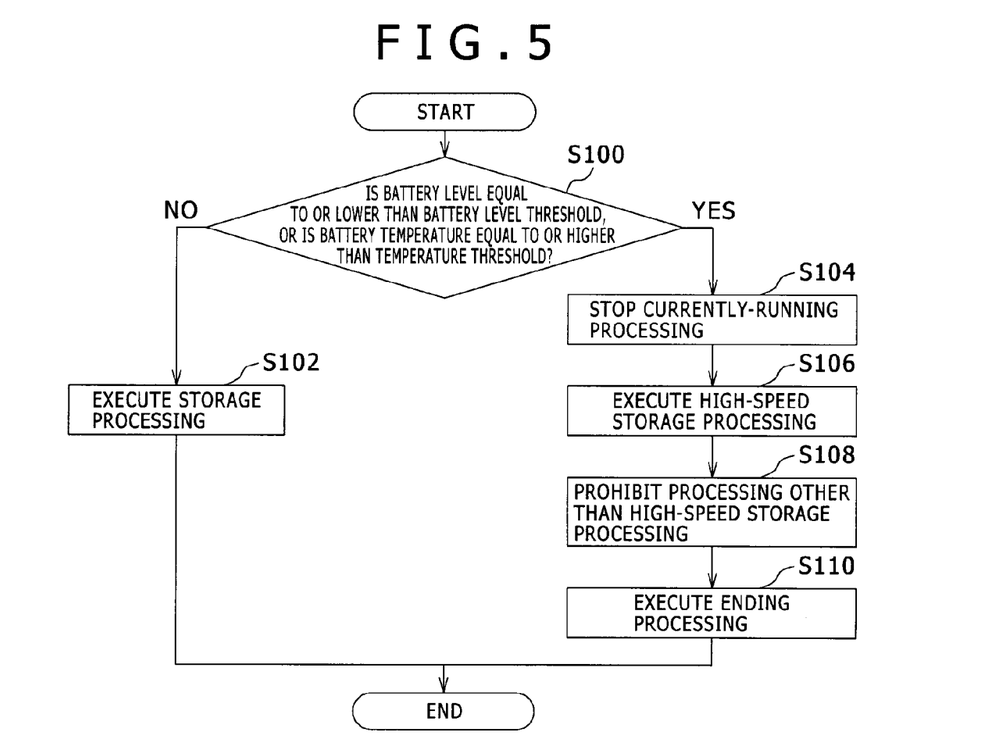
FIG. 5 shows a flowchart illustrating the operation in Embodiment 1 of the present invention.

Next, the operation of the present embodiment in the mobile ultrasonic diagnostic device will be explained by reference to the flowchart in FIG. 5.

(S100)

The temperature comparison unit 52 compares the temperature threshold stored in the temperature threshold storage unit 50 with the temperature of the battery 30 detected by the battery temperature detection unit 32, and if the temperature of the battery 30 is lower than the temperature threshold, the storage processing determination unit 36 (determination unit 58) determines that the battery 30 is in the normal state, and that the storage processing unit 38 can perform the storage processing. Then, the processing proceeds to S102. Conversely, if the temperature of the battery 30 is higher than the temperature threshold, the storage processing determination unit 36 (determination unit 58) determines that the battery 30 is in the abnormal state, and that the storage processing unit 38 cannot perform the storage processing. Then, the processing proceeds to S104.

The temperature threshold is set based on a temperature which accelerates deterioration of the battery 30. The temperature threshold can be set as desired via the operating unit 44 and stored in the temperature threshold storage unit 50. For example, the temperature threshold may be set at 50 degrees Celsius.

The battery temperature detection unit 32 detects the temperature of the battery 30 at predetermined time intervals. The predetermined time interval is an interval of several seconds, such as five seconds. Whenever the battery temperature detection unit 32 detects the temperature of the battery 30 at the predetermined time intervals, the temperature comparison unit 52 compares, at the predetermined time intervals, the temperature threshold stored in the temperature threshold storage unit 50 with the temperature of the battery 30 detected by the battery temperature detection unit 32.

The battery level comparison unit 56 compares the battery level threshold stored in the battery level threshold storage unit 54 with the battery level of the battery 30 detected by the battery level detection unit 34, and if the battery level of the battery 30 is higher than the battery level threshold, the storage processing determination unit 36 (determination unit 58) determines that the battery 30 is in the normal state, and that the storage processing unit 38 can perform storage processing. Then, the processing proceeds to S102. Conversely, if the battery level of the battery 30 is lower than the battery level threshold, the storage processing determination unit 36 (determination unit 58) determines that the battery 30 is in the abnormal state, and that the storage processing unit 38 cannot perform storage processing. Then, the processing proceeds to S104.

The battery level threshold is set based on the battery level of the battery 30 at which storage processing in the storage processing unit 38 is possible. The battery level of the battery 30 at which the storage processing unit 38 can perform storage processing is a battery level at which the storage processing unit 38 can perform storage processing; for example, for five minutes. The battery level threshold can be set as desired via the operating unit 44 and stored in the battery level threshold storage unit 54. For example, the battery level threshold can be set at 10 percent.

The battery level detection unit 34 detects the battery level of the battery 30 at the same time intervals as the predetermined time intervals to detect the temperature of the battery 30. Whenever the battery level detection unit 34 detects the battery level of the battery 30 at the predetermined time intervals, the battery level comparison unit 56 compares, at the predetermined time intervals, the battery level threshold stored in the battery level threshold storage unit 54 with the battery level of the battery 30 detected by the battery level detection unit 34.

In other words, the temperature comparison unit 52 and the battery level comparison unit 56 compare the temperature and the battery level of the battery 30 at the same predetermined time intervals. The battery level comparison unit 56 also determines the state of the battery 30 at the predetermined time intervals simultaneously. Accordingly, the state of the battery 30 can be determined every time using parameters of the battery 30.

(S102)

If the storage processing determination unit 36 determines that the temperature or the battery level of the battery 30 is in the normal state, the storage processing unit 38 can perform storage processing of data transfer or data writing. When the storage processing unit 38 completes storage processing of data transfer or data writing, the operation ends.

(S104)

If the storage processing determination unit 36 determines that the temperature or the battery level of the battery 30 is not in the normal state; that is, determines that it is in the abnormal state, the control unit 46 stops processing being executed in the components. For example, if storage processing of data transfer or data writing is being performed in the storage processing unit 38, that storage processing is stopped. When stopping the storage processing, the storage processing unit 38 stops the storage processing so as not to lose data which are being subjected to the storage processing. For example, after the storage processing being executed is completed, the storage processing unit 38 stops that storage processing.

If the storage processing determination unit 36 determines that the temperature or the battery level of the battery 30 is not in the normal state; that is, determine that it is in then abnormal state, and if ultrasound waves are being transmitted and received by the ultrasound transmission and reception control unit 18 when the storage processing unit 38 stops storage processing, the ultrasound transmission and reception control unit 18 stops transmitting and receiving ultrasound waves from/at the ultrasound probe 12, and the image display unit 26 freezes the image displayed thereon, or the image display unit 26 is caused not to display the image; that is, the image display unit 26 is turned off. When the storage processing unit 38 stops storage processing, it is also possible to stop image processing, such as trimming and image conversion in the image processing unit 24, and turn off the operating unit on the keyboard chassis 4. As such, it is possible to save consumption of the battery 30.

(S106)

If the storage processing determination unit 36 determines that the temperature or the battery level of the battery 30 is not in the normal state; that is, determines that it is in then abnormal state, the control unit 46 performs the storage processing in the high-speed storage unit 80.

If, before the storage processing unit 38 stops storage processing, the storage processing unit 38 is executing the storage processing, data relating to the storage processing in the storage processing unit 38 are stored in the high-speed storage unit 80, and after the data are stored in the high-speed storage unit 80, the storage processing unit 38 stops the storage processing.

For example, if an image (data) obtained from the tomographic image construction unit 22 or the image processing unit 24 are already stored in the high-speed storage unit 80, the data transfer unit 64, or the data writing unit 66, and if, for example, data stored in the high-speed storage unit 80 are transferred to the data transfer unit 64, while the data transfer unit 64 is transferring data, information of the data being transferred is temporarily copied into the high-speed storage unit 80. Then, after the information of the data being transferred is stored in the high-speed storage unit 80, the data transfer unit 64 stops transferring the data. Accordingly, no information of data is lost while it is being transferred. Further, if the data transfer unit 64 transfers the data per package (per group), after information of the data being transferred is copied into the high-speed storage unit 80 per package, the data transfer unit 64 stops transferring the data. Therefore, no information of data is lost while it is being transferred per package. The package is a certain piece of data which is composed of a plurality of pieces of data. That is, a package means a data group composed of a plurality of pieces of data.

Next, if the data obtained from the tomographic image construction unit 22 or the image processing unit 24 are not yet stored in the high-speed storage unit 80, the data transfer unit 64, or the data writing unit 66, while the data transfer unit 64 is transferring the data, information of the data being transferred and the data are temporarily copied into the high-speed storage unit 80. Then, after the information of the data being transferred and the data are copied into the high-speed storage unit 80, the data transfer unit 64 stops transferring the data. Therefore, no data are lost while they are being transferred. Further, if the data transfer unit 64 transfers data per package (per group), after information of the data being transferred and the data are copied into the high-speed storage unit 80 per package, the data transfer unit 64 stops transferring the data. Therefore, no data are lost while they are being transferred per package. The package is a certain piece of data which is composed of a plurality of pieces of data. That is, a package means a data group composed of a plurality of pieces of data.

Similarly, if an image (data) is already obtained from the tomographic image construction unit 22 or the image processing unit 24 and stored in the high-speed storage unit 80, the data transfer unit 64, or the data writing unit 66, and if, for example, the data stored in the high-speed storage unit 80 are written in the data transfer unit 64, while the data transfer unit 64 is transferring data, information of the data being transferred is temporarily copied into the high-speed storage unit 80. Then, after the information of the data being transferred is stored in the high-speed storage unit 80, the data writing unit 66 stops writing the data. Accordingly, no information of data is lost while it is being written. Further, if the data writing unit 66 writes the data per package, after the information of the data being written is copied into the high-speed storage unit 80 per package, the data transfer unit 64 stops writing the data. Therefore, no information of data is lost while it is being written per package.

Next, if the data obtained from the tomographic image construction unit 22 or the image processing unit 24 are not yet stored in the high-speed storage unit 80, the data transfer unit 64, or the data writing unit 66, while the data writing unit 66 is writing the data into the storage medium, information of the data being written and the data are temporarily copied into the high-speed storage unit 80. Then, after the information of the data being transferred and the data are copied into the high-speed storage unit 80, the data writing unit 66 stops writing the data. Therefore, no data are lost while they are being written. Further, if the data writing unit 66 writes the data per package, after the information of the data being written and the data are copied into the high-speed storage unit 80 per package, the data writing unit 66 stops writing the data. Therefore, no information of data is lost while it is being written per package.

Figure 6:
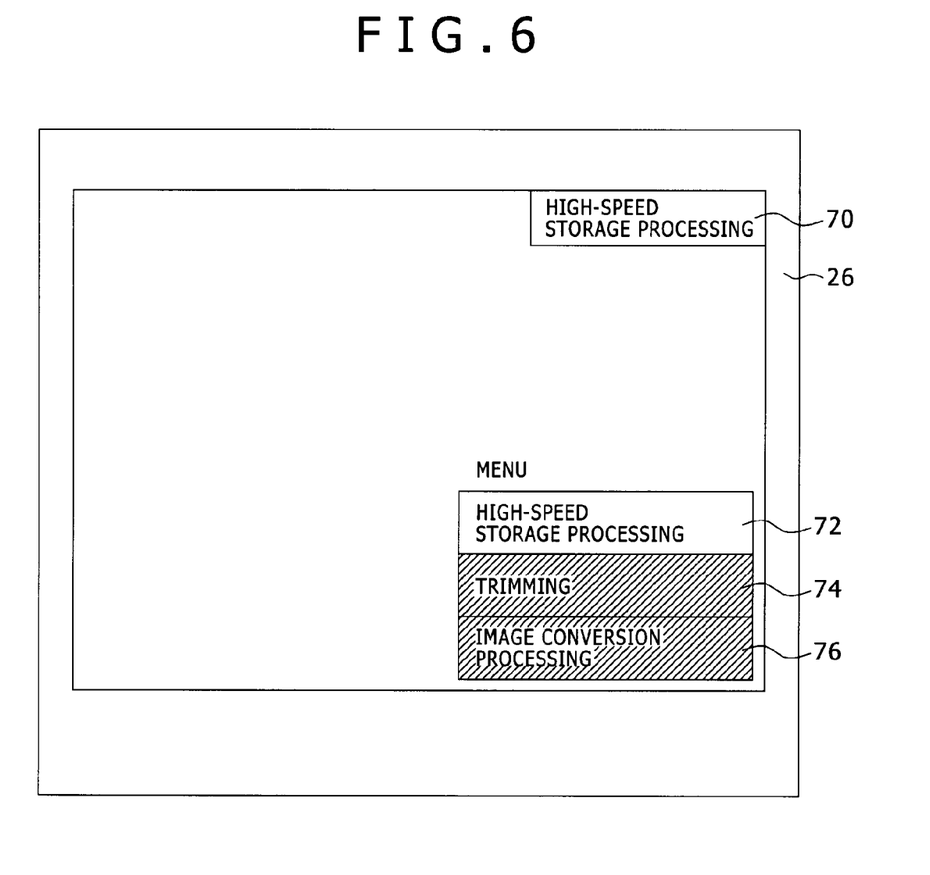
FIG. 6 shows one of display modes of the mobile ultrasonic diagnostic device according to the present invention.

While the high-speed storage unit 80 is performing storage processing, the storage processing determination unit 36 (determination unit 58) causes the image display unit 26 to display that high-speed storage processing is being executed. More specifically, as shown in FIG. 6, the image display unit displays a mark 70 indicating the high-speed storage processing. Thus, the operator can recognize that the high-speed storage processing is being executed, and that the temperature or the battery level of the battery 30 is not in the normal state.

(S108)

Then, the control unit 46 prohibits or stops processing by the components constituting the mobile ultrasonic diagnostic device other than the storage processing by the high-speed storage unit 80. The components other than the high-speed storage unit 80 become not able to perform processing.

More specifically, the image display unit 26 displays a menu in which executable processing and inexecutable processing are separately indicated, as shown in FIG. 6. For example, there is a high-speed storage processing menu 72 for high-speed storage processing which can be executed. There are a trimming menu 74 for trimming and an image conversion processing menu 76 for image conversion processing, and they are both shaded, which means that the image processing menus for the image processing unit 24 cannot be executed.

Thus, the operator can recognize that the high-speed storage processing can be executed, and that the components other than the high-speed storage unit 80 cannot execute processing.

(S110)

The high-speed storage unit 80 stores the storage processing of the storage processing unit 38 which was stopped. If there are a plurality of storage processing tasks which were stopped, the high-speed storage unit 80 stores each of the storage processing tasks. The components other than the high-speed storage unit 80 stop processing tasks being executed, and close applications. After the applications are closed, shutdown of the mobile ultrasonic diagnostic device is executed. The ending processing of the mobile ultrasonic diagnostic device is carried out in this manner. Accordingly, even if there is processing which is being executed, the mobile ultrasonic diagnostic device can be automatically shut down safely.

In S104 to S110, the control unit 46 can control execution of processing in the storage processing unit 38 according to a connection state of the AC adaptor 40. First, the adaptor connection detection unit 42 detects a connection state of the AC adaptor 42. More specifically, the adaptor connection detection unit 42 detects whether or not the AC adaptor 40 is connected to the electric outlet, based on electrical power supplied from the AC adaptor 40 to the components. If the AC adaptor 40 is connected to the electric outlet, and electrical power is supplied to the components, it is understood that the AC adaptor 40 supplies electrical power to the components and charges the battery 30. Therefore, if the AC adaptor 40 is connected to the electric outlet, because there is no possibility that the battery 30 will not be able to supply electrical power, the storage processing determination unit 36 (determination unit 58) determines to cause the storage processing unit 38 to perform all processing. Then, the storage processing unit 38 performs all processing. Similarly, the components other than the storage processing unit 38 execute all processing.

As described above, the present embodiment has the battery 30, the storage processing unit 38 which performs storage processing of data used in the mobile ultrasonic diagnostic device, the high-speed storage unit 80 which performs storage processing faster than the storage processing unit 38, and the storage processing determination unit 36 which determines storage processing based on the temperature or the battery level of the battery 30, and the storage processing unit 38 and the high-speed storage unit 80 perform storage processing based on the storage processing determined by the storage processing determination unit 36. Therefore, if there is a possibility that the battery 30 will not be able to supply electrical power, the mobile ultrasonic diagnostic device can be used safely.

Embodiment 2

Figure 7:
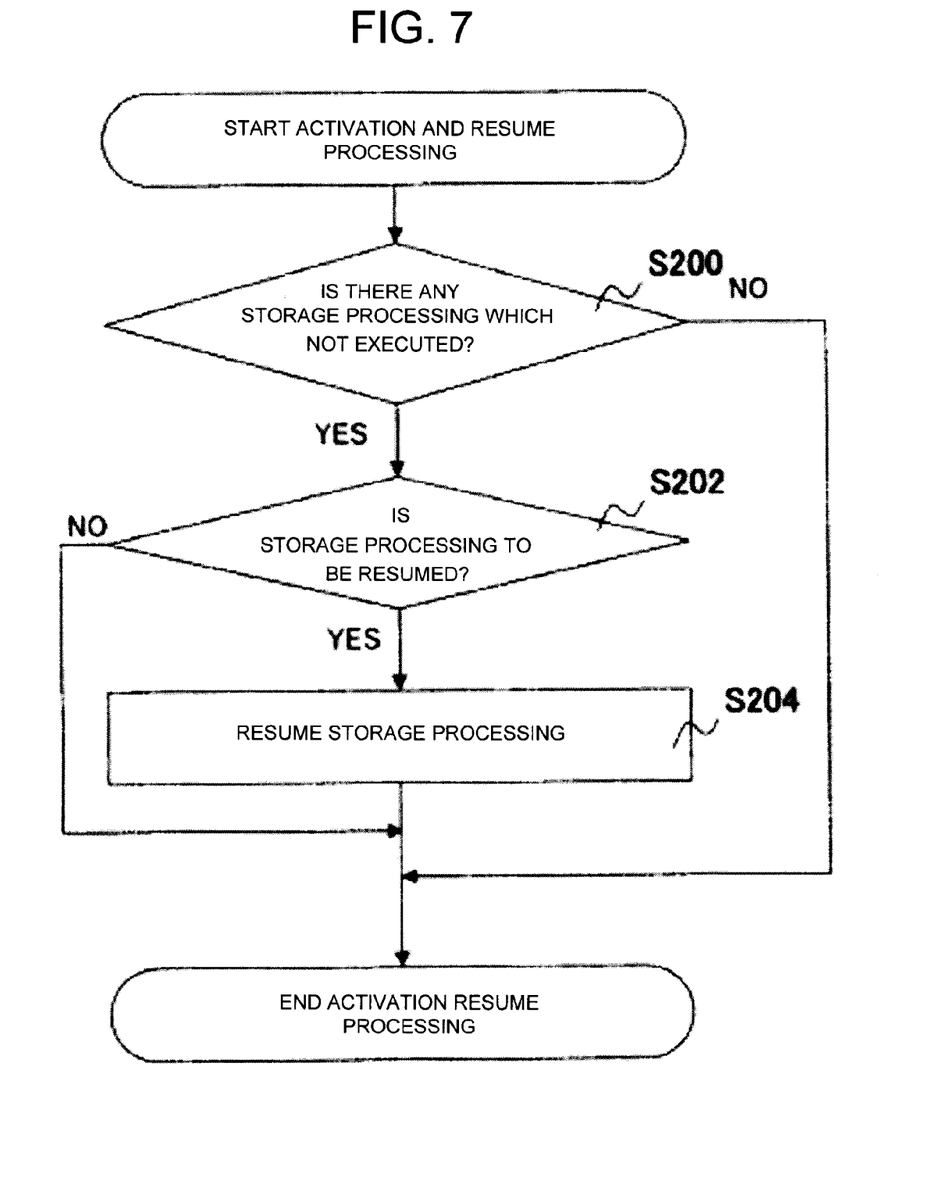
FIG. 7 shows a flowchart illustrating the operation in Embodiment 1 of the present invention.

Next, Embodiment 2 will be explained by reference to FIG. 7. Embodiment 2 differs from Embodiment 1 in that the storage processing of the storage processing unit 38 which was not executed is resumed by the storage processing unit 38 at the time of startup of the device.

(S200)

The high-speed storage unit 80 stores the storage processing in the storage processing unit 38, which was stopped in S104, and the data. The storage processing which was not stopped in the storage processing unit 38 and the data are read out from the high-speed storage unit 80, and the storage processing which was not executed is displayed on the image display unit 26. The operator can recognize the storage processing which was not executed.

If there is any processing which was not executed, the procedure proceeds to S202. If there is no processing which was not executed, the activation and resume processing ends.

(S202)

The operator selects whether or not to resume the processing which was not executed via the operating unit 44. If the operator wants to resume the storage processing in the storage processing unit 38, it is necessary that the condition that the battery level is equal to or lower than the battery level threshold, or the condition that the battery temperature is equal to or higher than the temperature threshold, is not satisfied in S100, or it is necessary for the AC adaptor 40 to be connected to the electric outlet to thereby supply electrical power to the components. For example, the operator can resume the storage processing in the storage processing unit 38 by connecting the AC adaptor 40 to the electric outlet.

(S204)

The storage processing stopped in the storage processing unit 38 in S104 is resumed. If, for example, while the data transfer unit 64 is transferring data which are already stored in the high-speed storage unit 80, that processing is stopped in S104, upon restart of data transfer which was stopped, information of data transfer which was stopped and the data to be transferred are read out from the high-speed storage unit 80, and the data transfer unit 64 transfers the data. If data transfer for a plurality of packages was stopped in the data transfer unit 64, information of data which was copied per package during transfer and the data to be transferred are read out from the high-speed storage unit 80, and the data transfer unit 64 transfers the data per package.

Figure 8:
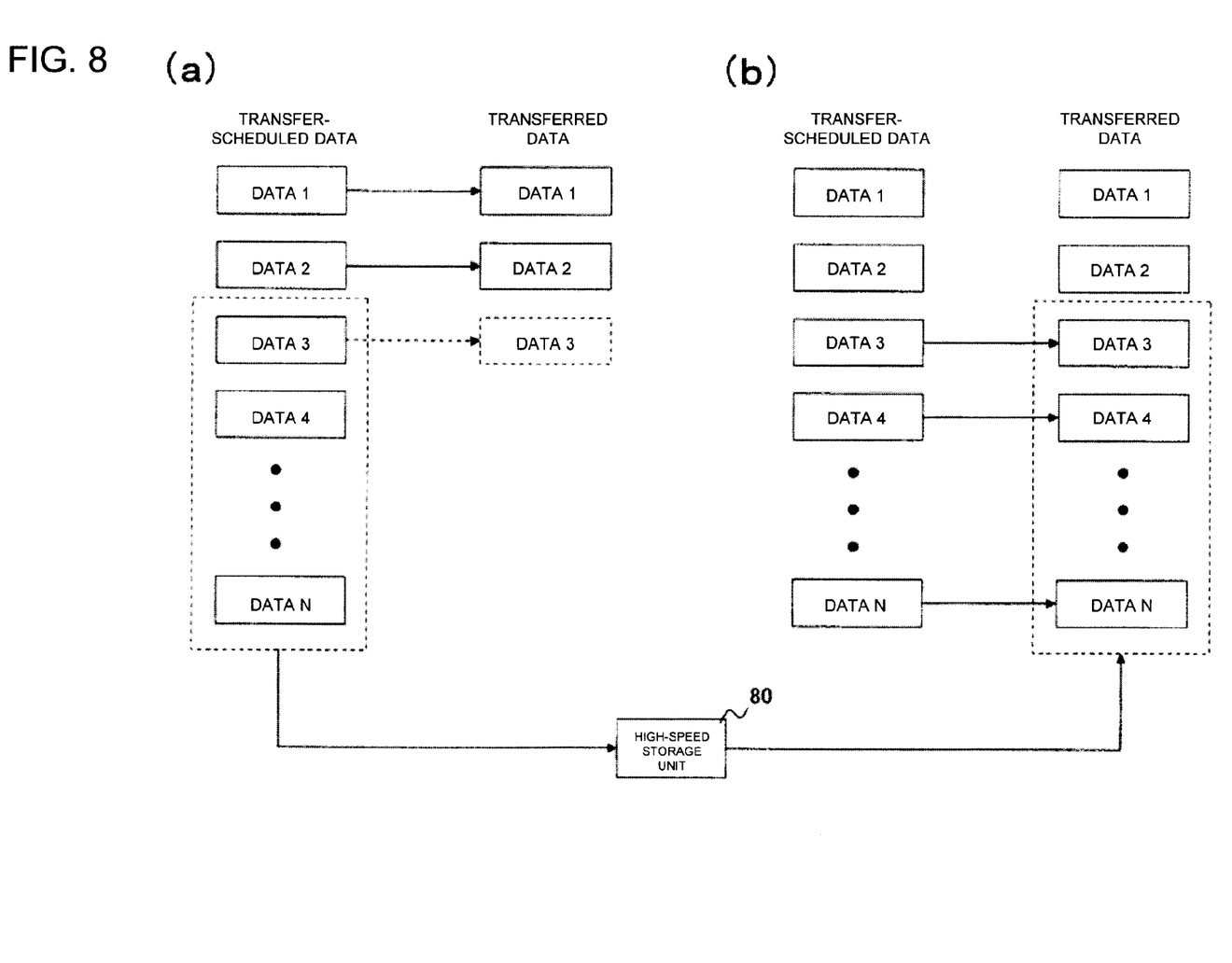
FIG. 8 shows the operation in Embodiment 2 of the present invention.
Figure 9:
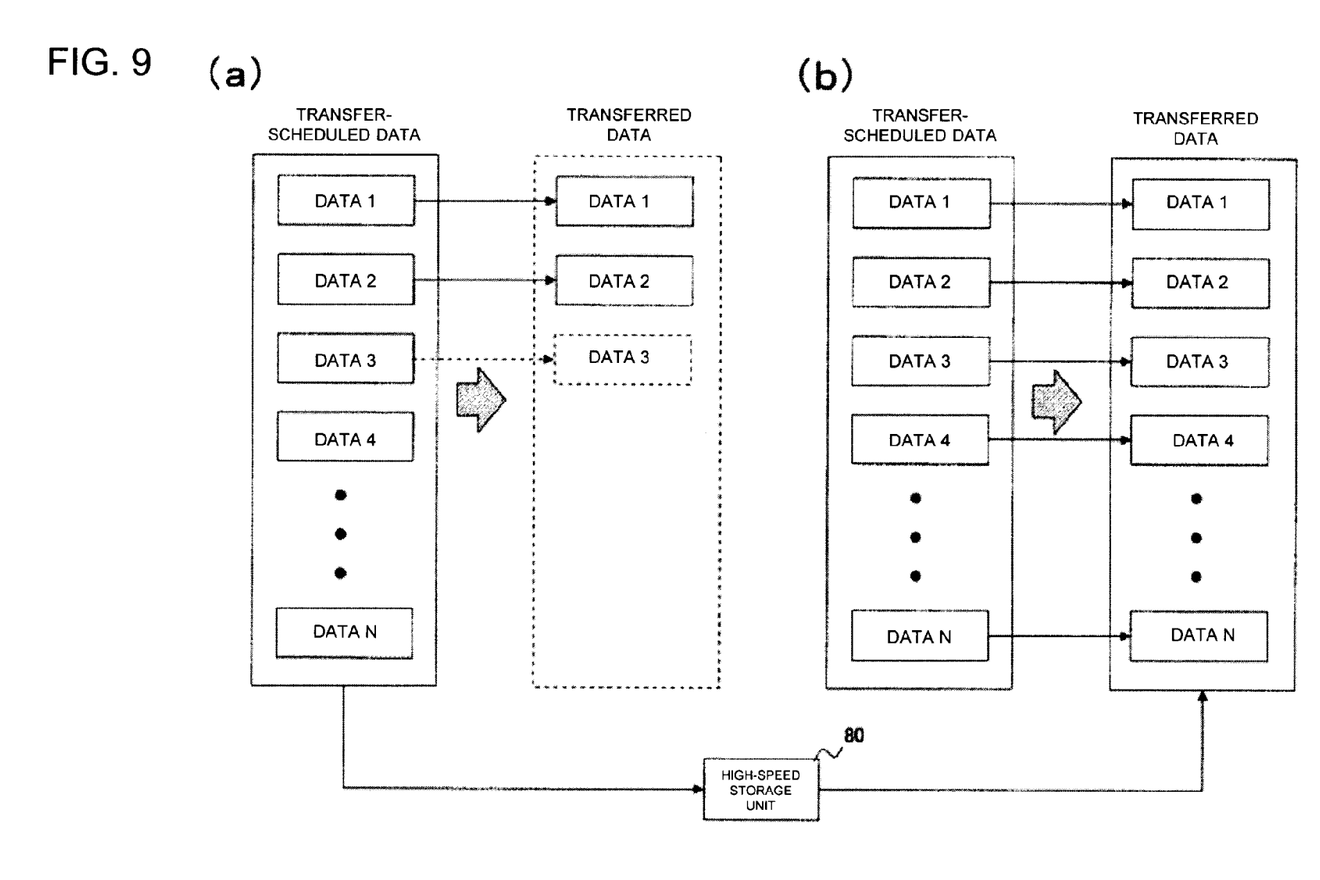
FIG. 9 shows the operation in Embodiment 2 of the present invention.

The above example will be explained in detail by reference to FIGS. 8 and 9. FIGS. 8 and 9 show the states of transfer-scheduled data which are scheduled to be transferred in the data transfer unit 64 of the storage processing unit 38, and transferred data which were already transferred to the devices outside the mobile ultrasonic diagnostic device by the data transfer unit 64.

As shown in FIG. 8(*a*), data 1 to data N are scheduled to be transferred by the data transfer unit 64, and data 1 and data 2 are already transferred to the devices outside the mobile ultrasonic diagnostic device. Here, it is assumed that, while data 3 is being transferred, the condition that the battery level is equal to or lower than the battery level threshold, or the condition that the battery temperature is equal to or higher than the temperature threshold is satisfied in S100. That is, data 3 to data N were not able to be transferred.

If the data are being transferred by the data transfer unit 64 under such conditions, information of data 3 being transferred is copied into the high-speed storage unit 80. Then, after data 3 being transferred is copied into the high-speed storage unit 80, the data transfer unit 64 stops transferring data 3. In addition, information of data 4 to data N which were not able to be transferred is also copied into the high-speed storage unit 80.

Then, upon restart of data transfer which was stopped, as shown in FIG. 8(b), data 3 which was stopped and information and data of data 4 to data N which were not able to be transferred are read out from the high-speed storage unit 80, and the data transfer unit 64 transfers data 3 to data N to the devices outside the mobile ultrasonic diagnostic device. As such, the data transfer unit 64 can transfer data 1 to data N without losing any data.

Further, if data are being transferred by the data transfer unit 64 as shown in FIG. 9(a), information of data being transferred is copied into the high-speed storage unit 80 per package (per group). After the data being transferred are copied into the high-speed storage unit 80 per package, the data transfer unit 64 stops transferring the data.

Here, as in FIG. 8(a), it is assumed that, while data 3 is being transferred, the condition that the battery level is equal to or lower than the battery level threshold, or the condition that the battery temperature is equal to or higher than the temperature threshold, is satisfied in S100. That is, data 3 to data N were not able to be transferred.

Information of data 1 to data N, including data 1 and data 2 which were transferred, is copied into the high-speed storage unit 80 as a package. Then, after the data of data 1 to data N are copied into the high-speed storage unit 80 as a package, the data transfer unit 64 stops transferring data 3.

Then, upon restart of data transfer which was stopped, as shown in FIG. 9(b), information of data transfer which was stopped and data 1 to data N provided as a package are read out from the high-speed storage unit 80, and the data transfer unit 64 transfers data 1 to data N to the devices outside the mobile ultrasonic diagnostic device. As such, the data transfer unit 64 can transfer data 1 to data N as a package without losing any data.

Similarly, if data writing was stopped in the data writing unit 66, information of data writing which was stopped and the data are read out from the high-speed storage unit 80, and the data writing unit 66 resumes writing the data into the recording medium, such as a DVD. If data writing for a plurality of packages was stopped in the data writing unit 66, information of data transfer which was stopped and the data are read out from the high-speed storage unit 80, and the data writing unit 66 resumes writing the data into the recording medium, such as a DVD, per package.

Further, if the storage processing unit 38 resumes storage processing, it is possible to cause the image display unit 26 to display items of the storage processing which have been resumed and inform the operator that the storage processing has been resumed. The operator can recognize that the stopped storage processing has been resumed.

Therefore, according to the present embodiment, it is possible to resume, at the time of startup, the storage processing which was not executed until the ending processing of the mobile ultrasonic diagnostic device.

Embodiment 3

Figure 10:
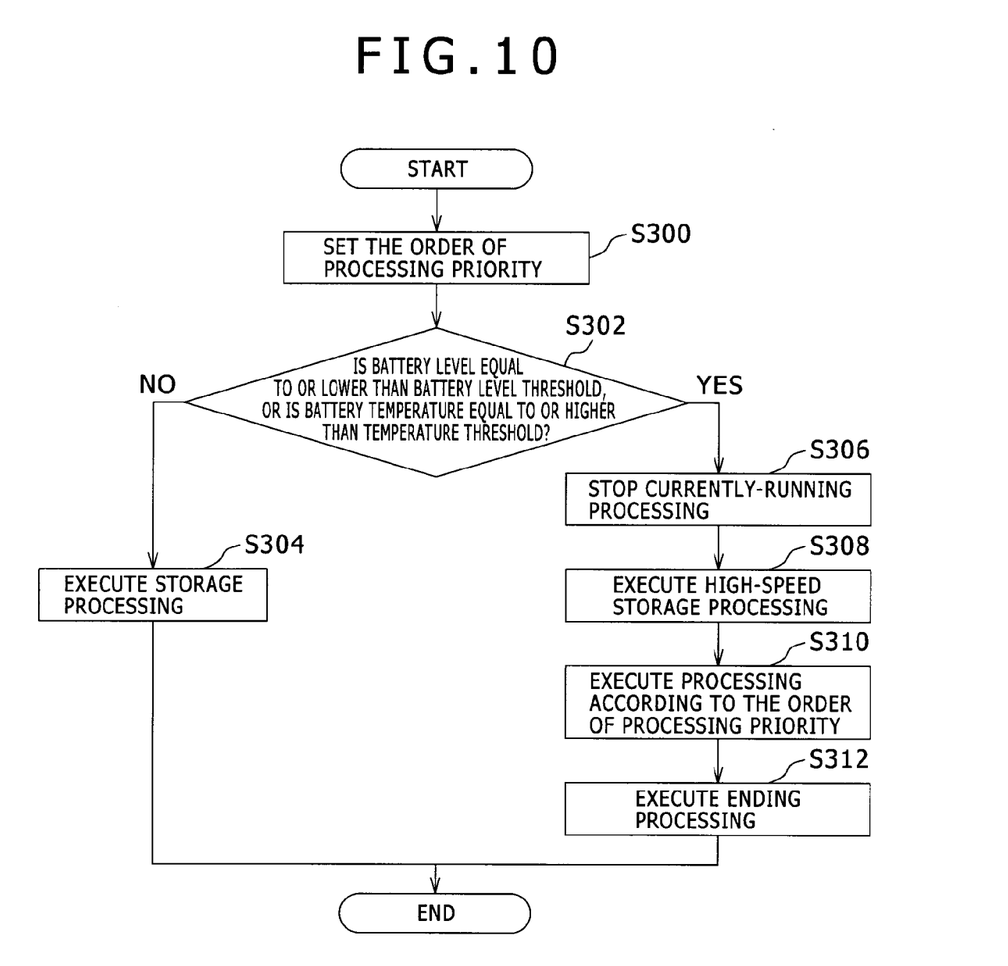
FIG. 10 shows a flowchart illustrating the operation in Embodiment 3 of the present invention.

Next, Embodiment 3 will be explained by reference to the flowchart in FIG. 10. Embodiment 3 differs from Embodiments 1 and 2 in that it has the operating unit 44 for setting an order of processing priority, and that the components constituting the mobile ultrasonic diagnostic device perform processing according to the order of processing priority.

Because the flowchart of FIG. 10 differs from the flowchart of FIG. 5 in S300 and S310, S300 and S310 will be explained below. There are S302 corresponding to S100, S304 corresponding to S102, S306 corresponding to S104, S308 corresponding to S106, and S312 corresponding to S110.

(S300)

First, the operator sets the order of processing priority for the components using the operating unit 44. Even if the condition that the battery level is equal to or lower than the battery level threshold, or the condition that the battery temperature is equal to or higher than the temperature threshold is satisfied in S302, it is possible for the components to perform processing which is set as the order of processing priority.

For example, storage processing in the high-speed storage unit 80 is set as the first priority. Trimming of the stored image in the image processing unit 24 is set as the second priority. Image conversion processing of the stores image in the image processing unit 24 is set as the third priority. The control unit 46 stores the relation between the order of processing priority set by the operating unit 44 and the components.

(S310)

The control unit 46 causes the components to execute processing according to the order or processing priority. Because the storage processing in the high-speed storage unit 80 has already been executed in S308 as the first priority, trimming of the stored image is carried out in the image processing unit 24, and then, image conversion processing of the stored image is carried out in the image processing unit 24. After execution of the processing in the components according to the order of processing priority, ending processing is executed in S312.

As such, according to the present embodiment, it is possible to perform processing according to the order of processing priority.

REFERENCE NUMERALS

2 BODY CHASSIS, 4 KEYBOARD CHASSIS, 6 DISPLAY CHASSIS, 8 CABLE, 10 TEST OBJECT, 12 ULTRASOUND PROBE, 14 TRANSMITTING UNIT, 16 RECEIVING UNIT, 18 ULTRASOUND TRANSMISSION AND RECEPTION CONTROL UNIT, 20 PHASING ADDITION UNIT, 22 TOMOGRAPHIC IMAGE CONSTRUCTION UNIT, 24 IMAGE PROCESSING UNIT, 26 IMAGE DISPLAY UNIT, 30 BATTERY, 32 BATTERY TEMPERATURE DETECTION UNIT, 34 BATTERY LEVEL DETECTION UNIT, 36 STORAGE PROCESSING DETERMINATION UNIT, 38 STORAGE PROCESSING UNIT, 40 AC ADAPTOR, 42 ADAPTOR CONNECTION DETECTION UNIT, 44 OPERATING UNIT, 46 CONTROL UNIT, 80 HIGH-SPEED STORAGE UNIT

The invention claimed is:
1. A mobile ultrasonic diagnostic device comprising:
a battery; and
a device that has a main processing function and includes:
a storage processing unit which is configured to perform storage processing of data used in the mobile ultrasonic diagnostic device, the storage processing including at least one of transferring the data and writing the data;

a high-speed storage unit which is configured to perform storage processing faster than the storage processing unit; and a storage processing determination unit which is configured to check a temperature and a battery level of the battery, is configured to determine storage processing for the storage processing unit when the temperature and the battery level of the battery is in a normal state, and is configured to determine storage processing for the high-speed storage unit to store the data related to the storage processing performed by the storage processing unit when at least one of the temperature or the battery level of the battery is not in the normal state.

2. The mobile ultrasonic diagnostic device according to claim 1, wherein the storage processing unit has at least one of a data transfer unit which is configured to transfer the data to a device outside the mobile ultrasonic diagnostic device and a data writing unit which is configured to write the data into a predetermined storage medium.

3. The mobile ultrasonic diagnostic device according to claim 2, wherein the data transfer unit is configured to transfer the data to the device outside the mobile ultrasonic diagnostic device via network communication.

4. The mobile ultrasonic diagnostic device according to claim 2, wherein the data writing unit is configured to write the data into any one of a CD, a DVD, a BD, a USB memory, and a USB hard disk.

5. The mobile ultrasonic diagnostic device according to claim 2, further comprising a high-speed storage medium into which the data are stored by the high-speed storage unit, wherein the high-speed storage medium has a larger capacity than a storage medium into which the data are written by the data writing unit.

6. The mobile ultrasonic diagnostic device according to claim 1, wherein, when the storage processing determination unit determines that the temperature or the battery level of the battery is not in the normal state, the storage processing unit stops storage processing.

7. The mobile ultrasonic diagnostic device according to claim 6, wherein, upon stop of the storage processing by the storage processing unit, the storage processing unit stops the storage processing so as not to lose the data before the data is stored by the high speed storage unit.

8. The mobile ultrasonic diagnostic device according to claim 6, further comprising an ultrasound transmission and reception control unit, which is configured to cause, upon stop of the storage processing by the storage processing unit, an ultrasound probe for transmitting and receiving ultrasonic waves to stop transmitting and receiving ultrasonic waves, and an image display unit, which is configured to freeze or turn off a displayed image upon stop of the storage processing by the storage processing unit.

9. The mobile ultrasonic diagnostic device according to claim 6, further comprising a high-speed storage medium into which the data are stored by the high-speed storage unit, wherein upon stop of the storage processing by the storage processing unit, the high-speed storage unit is caused to store the data relating to the storage processing in the storage processing unit.

10. The mobile ultrasonic diagnostic device according to claim 6, wherein, at the time of startup of the mobile ultrasonic diagnostic device, the storage processing unit resumes storage processing which was not previously executed in the storage processing unit using the data stored by the high speed storage unit.

11. The mobile ultrasonic diagnostic device according to claim 1, further comprising a control unit which is configured to prohibit or stop processing by components constituting the mobile ultrasonic diagnostic device other than the storage processing by the high-speed storage unit.

12. The mobile ultrasonic diagnostic device according to claim 1, further comprising an adaptor connection detection unit which is configured to detect a connection state of an AC adaptor, wherein, when the AC adaptor is connected to an electric outlet, the storage processing determination unit determines to cause the storage processing unit to execute all processing.

13. The mobile ultrasonic diagnostic device according to claim 1, further comprising an operating unit which is configured to set an order of processing priority, wherein the components constituting the mobile ultrasonic diagnostic device are configured to perform processing according to the order of processing priority.

14. The mobile ultrasonic diagnostic device according to claim 1, wherein:

the storage processing determination unit comprises:
 a temperature threshold storage unit which is configured to store a temperature threshold of the battery;
 a temperature comparison unit which is configured to compare the temperature threshold stored in the temperature threshold storage unit with a temperature of the battery detected by a temperature detection unit which detects the temperature of the battery;
 a battery level threshold storage unit which is configured to store a battery level threshold of the battery; and
 a battery level comparison unit which is configured to compare the battery level threshold stored in the battery level threshold storage unit with a battery level detected by a battery level detection unit which detects the battery level of the battery.

15. The mobile ultrasonic diagnostic device according to claim 14, wherein the temperature comparison unit and the battery level comparison unit respectively compare the temperature and the battery level of the battery with the thresholds at the same predetermined time intervals.

* * * * *